United States Patent [19]

Garlaschelli et al.

[11] 4,401,675
[45] Aug. 30, 1983

[54] FUNGICIDAL CARBAZATES

[75] Inventors: Luigi Garlaschelli, Pavia; Franco Gozzo, San Donato Milanese; Luigi Mirenna, Milan, all of Italy

[73] Assignee: Montedison S.p.A., Milan, Italy

[21] Appl. No.: 308,137

[22] Filed: Oct. 2, 1981

[30] Foreign Application Priority Data

Oct. 3, 1980 [IT] Italy ............................. 25100 A/80

[51] Int. Cl.$^3$ .................. A01N 43/08; C07C 125/073
[52] U.S. Cl. .................................... 424/285; 424/300; 549/487; 560/24; 560/30; 560/27; 560/29
[58] Field of Search ...................... 560/24, 30, 27, 29; 71/3; 424/300, 285; 549/487

[56] References Cited

U.S. PATENT DOCUMENTS 4,325,966  4/1982  Punja ..................................... 560/24

FOREIGN PATENT DOCUMENTS 2184974  12/1973  France .

OTHER PUBLICATIONS

Wagner et al., Synthetic Organic Chem., John Wiley & Sons, Inc., N.Y., pp. 567–568, (1965).
Nesynov et al., Chem. Absts., 83, 127289(v), 1975.
Baumgarten et al., J. Org. Chem., 41(24), pp. 3805–3811, (1976).

*Primary Examiner*—Bernard Helfin

[57] ABSTRACT

Alkyl 3-aryl-3-acyl-2-methyl-carbazates which are highly effective fungicides in the fight against fungus infections in useful plants are disclosed, as is the use thereof in fighting phytopathogenous fungi.

13 Claims, No Drawings

FUNGICIDAL CARBAZATES

BACKGROUND OF THE INVENTION

As far as we are aware, the only example of fungicidal carbazates cited in literature is represented by French patent application No. 2,184,974 (Bayer).

However, the carbazates described in the said French patent application belong to the class of 3-aryl-carbazates and, therefore, are exclusively monosubstituted.

THE PRESENT INVENTION

One object of this invention is to provide new multi-substituted carbazates which exhibit exceptionally high fungicidal activity, both preventive and curative, and which have good systemic characteristics.

This and other objects are achieved by the present invention which provides carbazates of the formula

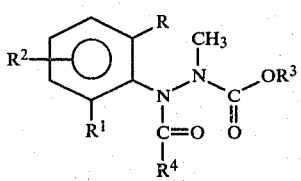

(I)

wherein

R, $R^1$ and $R^2$, the same or different, represent H, a halogen, a $C_1$–$C_4$ alkyl, or a $C_1$–$C_4$ alkoxyl;

$R^3$ is a $C_1$–$C_4$ alkyl;

$R^4$ is a $C_1$–$C_4$ alkyl optionally substituted by one or more halogen atoms or $C_1$–$C_4$ alkoxyls; phenyl optionally substituted by one or more halogen atoms, $C_1$–$C_4$ alkyl groups or $C_1$–$C_4$ alkoxyl groups; benzyl; the group $CH_2COCH_3$; or a heterocyclic group having 5 or 6 terms containing 1 to 3 heteroatoms.

The compounds of formula I can be prepared according to conventional techniques. Referring to Scheme I, which follows, 3-aryl-carbazates (III, $R^5$ is H) or 2-methyl-3-aryl-carbazates (III, $R^5$ is $CH_3$) are starting products useful in the synthesis. Said compounds can be prepared by condensing an aryl-hydrazine (II, $R^5$ is H or $CH_3$) with an alkyl-haloformate in an inert solvent and in the presence of a haloid acid-accepting base, as described, for example, in Berichte 33, 458 1900).

Intermediates III so obtained are then condensed with the suitable acyl-halide in an inert solvent and in the presence of a base.

The methyl group in position 2 may already be present in the starting compound which, in such case, is a 2-methyl-3-aryl-carbazate (III, $R^5$ is $CH_3$), or it may be introduced into intermediate IV, obtained from the condensation with the acyl halide, by means of reaction with methyl halide in the presence of a strong base.

Scheme 1

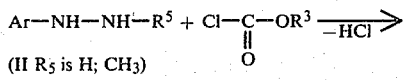

(II $R_5$ is H; $CH_3$)

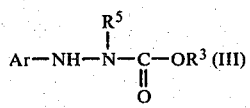

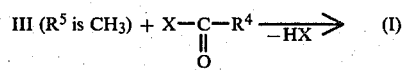  (I)

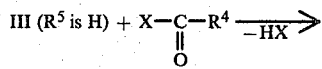

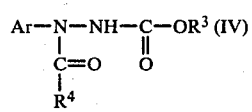 (IV)

IV + $CH_3X$ $\xrightarrow{-HX}$ (I)

[Ar is 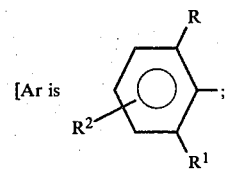 ;

X is Cl, Br or I; R, $R^1$, $R^2$, $R^3$ and $R^4$ have the same meanings as in formula I].

The compounds of formula III in which $R^5$ is $CH_3$ are new, per se.

Thus, a further object of the present invention consists in providing the compounds of formula:

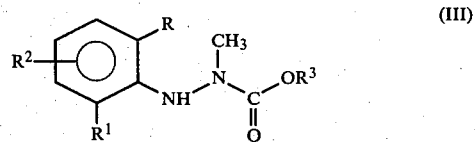

(III)

wherein R, $R^1$, $R^2$ and $R^3$ have the same meanings as in general formula I.

As already disclosed herein, the compounds of general formula I exhibit a high fungicidal activity towards phytopathogenous fungi. The action exerted by them is both of preventive nature (in that it prevents the infection from arising) and of curative nature (when the infection has set in.)

Furthermore, they possess good systemic characteristics (i.e., they are carried to the various parts of the plants). The compounds of general formula I prove also to be compatible with the plants to be protected against the fungus infection.

The most important class of phytopathogenous fungi which can be successfully fought by using the fungicidal compounds of formula I is the fungi classified as Phycomycetes and comprising Plasmopara spp, Peronospora spp, Pseudoperonospora spp, and Phythium spp.

In consequence, the compounds of the invention are effective in fighting fungus infections of useful plants such as vines, tomatos, tobacco, potatoes and other agrarian cultivations.

For practical utilization in agriculture, the fungicides of formula I may be employed as such or in the form of suitable compositions.

Said compositions consist of one or more compounds of formula I as active substance, of a solid or liquid vehicle and, optionally, of surfactants and other additives of the kind often used in formulating compositions for agricultural application.

The fungicidal compounds of this invention can be formulated, according to known techniques, in the form of emulsifiable liquids, dry powders, wettable powders, etc. If desired, other active substances, such as insecticides, other fungicides, phyto growth regulators, etc., can be added to the compositions or formulations.

The amount of compound of formula I necessary to obtain a good protection of the agrarian cultivations from fungus infections depends on various factors such as, for example, the relative effectiveness of the compound of formula I employed, the type of composition or formulation, the type of fungus to be fought and the extent of the infection, the type of cultivation to be protected, and on climatic and environmental factors.

The following examples are given to illustrate the present invention in more detail and are not intended to be limiting.

EXAMPLE 1

Preparation of methyl 3-(2,6-dimethylphenyl)-3-methoxyacetyl-2-methyl-carbazate (compound No. 4, Table I).

A—Preparation of methyl 3-(2,6-dimethylphenyl)-carbazate.

18 g of 2,6-dimethylphenyl-hydrazine and 14 g of triethylamine were dissolved in 150 ml of ethyl ether. Keeping the temperature at 0° C., 12.5 g of methyl chloroformate were added dropwise to the solution. Precipitation of the chlorohydrate of triethylamine was observed.

After one night at room temperature, the reaction mixture was washed with water (2×100 ml), and then anhydrified on anhydrous $Na_2SO_4$, whereupon the solvent was removed by evaporation.

13 g of a solid product were so obtained, which, after crystallization from ligroin, had a melting point of 75°–78° C.

B—Preparation of methyl 3-(2,6-dimethylphenyl)-3-methoxyacetyl-carbazate.

3 g of methyl-3-(2,6-dimethylphenyl)-carbazate were dissolved in 40 ml of methylene chloride ($CH_2Cl_2$). While stirring at room temperature, 1.7 g of methoxyacetyl chloride were gradually dropped into the solution. The reaction mixture was stirred at room temperature for 3 hours. It was then washed with 20 ml of $H_2O$, 30 ml of a solution of $NaHCO_3$ at 5% and 30 ml of $H_2O$. It was anhydrified on anhydrous $Na_2SO_4$ and the solvent was removed by evaporation.

3 g of a light solid were so obtained, which, after crystallization from ethyl acetate/ligroin in a ratio of 2:3, had a melting point of 165°–169° C.

C—Preparation of methyl 3-(2,6-dimethylphenyl)-3-methoxyacetyl-2-methyl-carbazate.

5 g of methyl 3-(2,6-dimethylphenyl)-3-methoxyacetyl-carbazate were dissolved in 60 ml of anhydrous tetrahydrofuran. The solution was gradually dropped at 20° C. into a suspension of 0.53 g of NaH in 30 ml of anhydrous tetrahydrofuran. A slight exothermy was observed.

After a 2-hour stirring at 20° C., 3.2 g of methyl iodide were added, and the stirring was continued for 24 hours at room temperature.

100 ml of ethyl ether were then added, whereupon the reaction was stopped by cautiously adding water.

The organic phase was separated and the aqueous phase was extracted again with methylene chloride (2×50 ml). The united organic phases were anhydrified on anhydrous $Na_2SO_4$ and the solvents were removed by evaporation. A residue (5 g) was obtained which was purified by chromatography on a silica gel column (eluent: ethyl acetate/toluene in a 1:1 ratio).

2.5 g of the desired product (C) were obtained, which slowly crystallized to a light solid having a melting point of 66°–69° C.

EXAMPLE 2

By operating analogously to Example 1, the compounds reported in the following Table I were prepared.

TABLE I

| Compound No. | Compounds of Formula I | | | | | m.p.[a] 99–104 | IR[b] (cm$^{-1}$) |
|---|---|---|---|---|---|---|---|
| | R | $R^1$ | $R^2$ | $R^3$ | $R^4$ | | |
| 1 | $CH_3$ | $CH_3$ | H | $CH_3$ | $CH_2Cl$ | oil | 1680–1720 |
| 2 | H | H | H | $CH_3$ | $CH_2OCH_3$ | oil | 1690–1720 |
| 3 | H | H | H | $CH_3$ | $CH_3$ | oil | 1680–1720 |
| 4[c] | $CH_3$ | $CH_3$ | H | $CH_3$ | $CH_2OCH_3$ | 66–9 | 1690–1720 |
| 5 | $CH_3$ | $CH_3$ | H | $CH_3$ | $CF_3$ | 99–104 | 1700–1730 |
| 6 | $CH_3$ | $CH_3$ | H | $CH_3$ | $CH_2-C_6H_5$ | oil | 1680–1720 |
| 7 | $CH_3$ | $CH_3$ | H | $CH_3$ | 2-furyl | 129–31 | 1660–1740 |
| 8 | $CH_3$ | $CH_3$ | H | $CH_3$ | $CH_2-CO-CH_3$ | oil | 1630–1675–1720 |

Notes to Table I
[a]Melting points were not corrected
[b]Only the bands corresponding to $\nu C = O$ are reported
[c]Preparation of compound No. 4 is described in Example 1

EXAMPLE 3

Curative activity on vine Peronospora [*Plasmopara viticola* (B. et C.) Berl et de Toni].

The leaves of cv. Dolcetto vine plants, cultivated in pots in a conditioned room at 25° C. and 60% relative humidity, were sprayed, on their lower faces, with an aqueous suspension of *Plasmopara viticola* conides (200,000 conides/cc).

After a 24-hour residence time in a humidity-saturated room at 21° C., the plants' leaves were sprayed on both faces with the products being tested in a hydroacetonic solution at 20% of acetone (vol./vol.).

At the conclusion of the incubation period (7 days), the extent or degree of infection was evaluated at sight according to the indexes of the following evaluation scale:

0=no control; infection like the one of the check (infected and not treated plants)

1 = 1 to 20% of infection decrease
2 = 20 to 60% of infection decrease
3 = 60 to 90% of infection decrease
4 = infection decrease above 90%.

The results obtained are recorded in following Table II.

TABLE II

Curative Activity on Vine Peronospora in a Dose of 0.5%

| Compound No. (See Table I) | Fungicidal Activity |
|---|---|
| 1 | 4 |
| 2 | 4 |
| 3 | 4 |
| 4 | 4 |
| 5 | 4 |
| 6 | 4 |
| 7 | 4 |
| 8 | 4 |

What we claim is:

1. Compounds of general formula

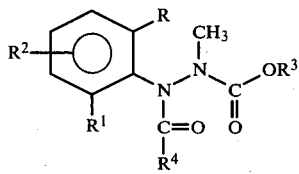

(I)

in which

R, $R^1$ and $R^2$ (like or unlike one another) are H, a halogen, an alkyl $C_1$–$C_4$, an alkoxyl $C_1$–$C_4$;

$R^3$ is an alkyl $C_1$–$C_4$;

$R^4$ is an alkyl $C_1$–$C_4$ optionally substituted by one or more halogen atoms or alkoxyls $C_1$–$C_4$; a phenyl optionally substituted by one or more halogen atoms, alkyl groups $C_1$–$C_4$ or alkoxyl groups $C_1$–$C_4$; a benzyl; the group $CH_2COCH_3$; or furyl.

2. The compounds according to claim 1, in which R and $R^1$ are $CH_3$ and $R^2$ is H.

3. A compound according to claim 1 and which is methyl 3-(2,6-dimethylphenyl)-3-chloroacetyl-2-methyl-carbazate.

4. A compound according to claim 1 and which is methyl 3-(2,6-dimethylphenyl)-3-methoxyacetyl-2-methyl-carbazate.

5. A compound according to claim 1 and which is methyl 3-(2,6-dimethylphenyl)-3-trifluoroacetyl-2-methyl-carbazate.

6. A compound according to claim 1 and which is methyl 3-(2,6-dimethylphenyl)-3-phenylacetyl-2-methyl carbazate.

7. A compound according to claim 1 and which is methyl 3-(2,6-dimethylphenyl)-3-acetoacetyl-2-methyl-carbazate.

8. A compound according to claim 1 and which is methyl 3-(2,6-dimethylphenyl)-3-(2-furoyl)-2-methyl-carbazate.

9. The compounds according to claim 1, in which R, $R^1$ and $R^2$ are H.

10. The compound methyl 3-phenyl-3-methoxyacetyl-2-methyl-carbazate.

11. The compound methyl 3-phenyl-3-acetyl-2-methyl-carbazate.

12. A method of fighting fungus infections of useful plants, consisting in distributing on the plants, when the infection is not yet in course or when the infection is already in progress, a fungicidally effective amount of at least one compound according to claim 1, as such, or in the form of a suitable formulation.

13. A fungicidal formulation containing, as active substance, a fungicidally effective amount of at least one compound according to claim 1, and an inert carrier.

* * * * *